(12) United States Patent
Shareef et al.

(10) Patent No.: US 10,857,171 B2
(45) Date of Patent: Dec. 8, 2020

(54) PHARMACEUTICAL COMPOSITIONS

(71) Applicant: WOCKHARDT LIMITED, Aurangabad (IN)

(72) Inventors: Mohammad Ajmal Shareef, Bihar (IN); Mrutunjaya Sahu, Orissa Ganjam (IN); Ajaykumar Handa, Aurangabad (IN)

(73) Assignee: WOCKHARDT LIMITED, Aurangabad (IN)

( * ) Notice: Subject to any disclaimer, the term of this patent is extended or adjusted under 35 U.S.C. 154(b) by 38 days.

(21) Appl. No.: 15/550,779

(22) PCT Filed: Jan. 12, 2017

(86) PCT No.: PCT/IB2017/050155
§ 371 (c)(1),
(2) Date: Aug. 13, 2017

(87) PCT Pub. No.: WO2017/122147
PCT Pub. Date: Jul. 20, 2017

(65) Prior Publication Data
US 2018/0028548 A1 Feb. 1, 2018

(30) Foreign Application Priority Data
Jan. 12, 2016 (IN) .............................. 201621001033

(51) Int. Cl.
*A61K 31/7048* (2006.01)
*A61K 9/20* (2006.01)

(52) U.S. Cl.
CPC ........ *A61K 31/7048* (2013.01); *A61K 9/2009* (2013.01); *A61K 9/2013* (2013.01); *A61K 9/2027* (2013.01); *A61K 9/2054* (2013.01); *Y02A 50/30* (2018.01)

(58) Field of Classification Search
CPC .............. A61K 31/7048; A61K 9/2009; A61K 9/2013; A61K 9/2027; A61K 9/2054; Y02A 50/478
See application file for complete search history.

(56) References Cited

U.S. PATENT DOCUMENTS

2008/0113020 A1* 5/2008 Desesquelle ......... A61K 9/2054
424/464
2014/0005133 A1* 1/2014 Trivedi ................ C07D 417/04
514/29

FOREIGN PATENT DOCUMENTS

| WO | WO/2002/016380 | 2/2002 |
| WO | WO/2002/050092 | 6/2002 |
| WO | WO/2012/076989 | 6/2012 |

OTHER PUBLICATIONS

Jim O'Neil's publication, 2016. UK government report on antimicrobial resistance (AMR).
Nature Biotechnology vol. 36 No. 7 Jul. 2018, p. 555.
Borst, title: Stability of Five Beta-lactam Antibiotics in Sterile Water for Injection and Stored in Plastic Syringes, Ph.D., dissertation, Jun. 1984.
Kucher—book (3 volumes—Kucers' The Use of Antibiotics: A Clinical Review of Antibacterial, Antifungal, Antiparasitic, and Antiviral Drugs. Published Oct. 2, 2017. A table of contents is filed.

* cited by examiner

*Primary Examiner* — Matthew P Coughlin
*Assistant Examiner* — Thurman Wheeler
(74) *Attorney, Agent, or Firm* — Bio Intellectual Property Services LLC (Bio IPS); O. (Sam) Zaghmout

(57) ABSTRACT

The stable pharmaceutical compositions comprising a compound of Formula (I) or a stereoisomer or a pharmaceutically acceptable derivative thereof are disclosed.

Formula (I)

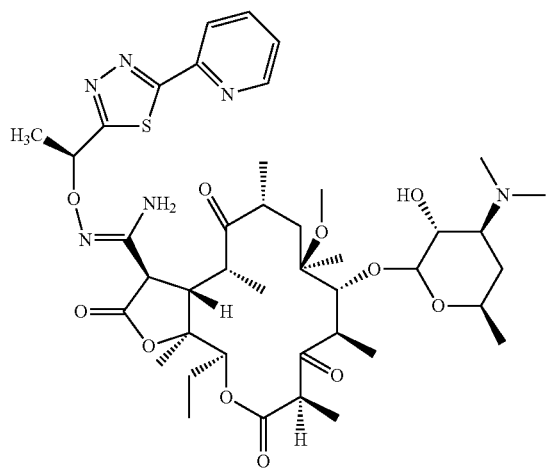

3 Claims, No Drawings

PHARMACEUTICAL COMPOSITIONS

RELATED PATENT APPLICATIONS

This application claims benefit of Indian Patent Application No. 201621001033 filed on Jan. 12, 2016, the disclosures of which are incorporated herein by reference in its entirety as if fully rewritten herein.

FIELD OF THE INVENTION

The invention relates to pharmaceutical compositions comprising an antibacterial agent, a process for preparing such compositions, and use of such compositions in treating bacterial infections.

BACKGROUND OF THE INVENTION

Bacterial infections continue to remain one of the major causes of human diseases. A variety of antibacterial compounds are currently used in treating infections caused by bacteria. PCT International Patent Application Number PCT/IB2011/050464 discloses several compounds having antibacterial activity, including the compound of Formula (I).

Formula (I)

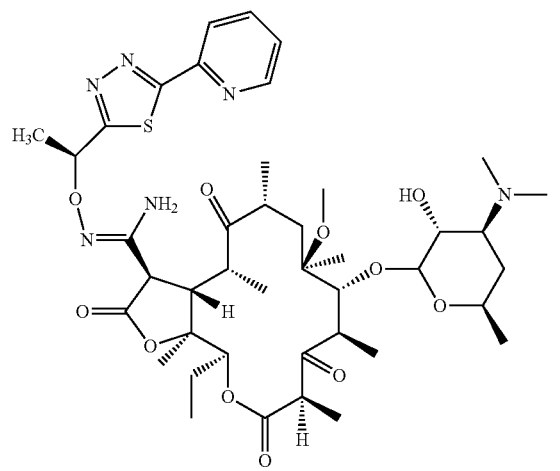

The present invention describes pharmaceutical compositions comprising a compound of Formula (I) or a pharmaceutically acceptable derivative thereof; a process for preparation of such compositions; and use of such compositions in treating bacterial infections.

SUMMARY OF THE INVENTION

Accordingly, there are provided solid pharmaceutical compositions comprising a compound of Formula (I) or a pharmaceutically acceptable derivative thereof.

Formula (I)

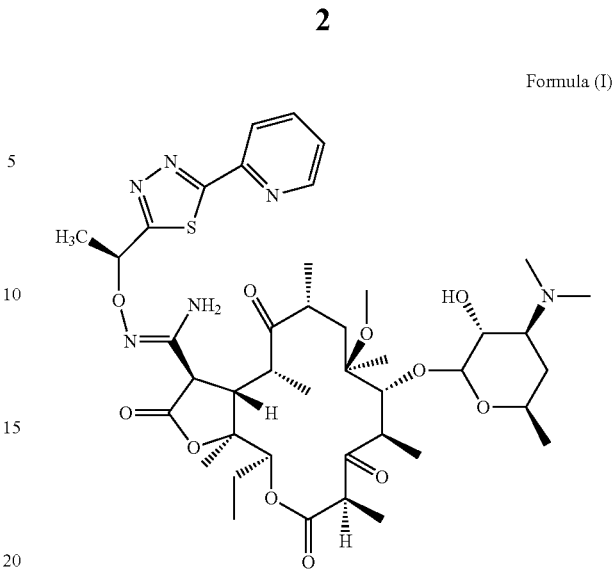

In one general aspect, there are provided solid pharmaceutical compositions comprising a compound of Formula (I) or a pharmaceutically acceptable derivative thereof in form of tablets.

In another general aspect, there is provided a process for preparing a tablet dosage form a compound of Formula (I) or a pharmaceutically acceptable derivative thereof.

In another general aspect, the compositions according to the invention are used in treating bacterial infections.

In another general aspect, there is provided a method for treating bacterial infection in a subject, said method comprising administering to said subject a therapeutically effective amount of a pharmaceutical composition according to the invention.

The details of one or more embodiments of the invention are set forth in the description below. Other features, objects and advantages of the invention will be apparent from the following description, including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety.

The invention discloses solid pharmaceutical compositions comprising a compound of Formula (I) or a pharmaceutically acceptable derivative thereof; a process for preparing such compositions and use of such compositions in treating bacterial infections.

Formula (I)

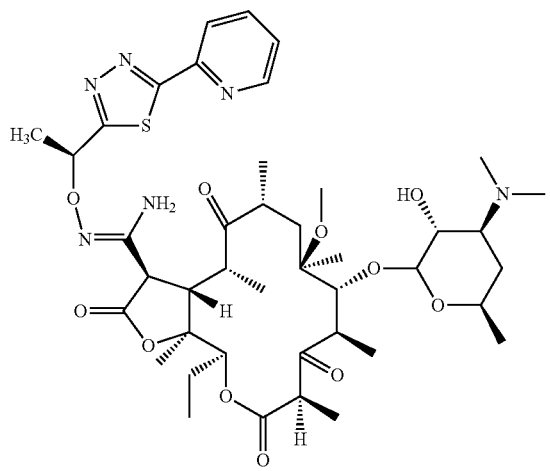

The term "pharmaceutically acceptable derivative" as used herein refers to and includes any pharmaceutically acceptable salt, pro-drugs, metabolites, esters, ethers, hydrates, polymorphs, solvates, complexes and adducts of a compound described herein which, upon administration to a subject, is capable of providing (directly or indirectly) the parent compound. For example, the term "a compound of Formula (I) or a pharmaceutically acceptable derivative thereof" includes all derivatives of the compound of Formula (I) (including pharmaceutically acceptable salts, pro-drugs, metabolites, esters, ethers, hydrates, polymorphs, solvates, complexes and adducts) which, upon administration to a subject, are capable of providing (directly or indirectly) the compound of Formula (I). Likewise, the term "Citric acid or a pharmaceutically acceptable derivative thereof" includes citric acid and all derivatives of citric acid (including pharmaceutically acceptable salts, pro-drugs, metabolites, esters, ethers, hydrates, polymorphs, solvates, complexes and adducts), which upon administration to a subject, are capable of providing (directly or indirectly) citric acid. Typical, non-limiting examples of pharmaceutically acceptable derivatives of citric acid include citric acid monohydrate, sodium citrate di hydrate and a like.

The term "pharmaceutically acceptable salt" as used herein refers to one or more salts of a given compound which possesses the desired pharmacological activity of the free compound and which are neither biologically nor otherwise undesirable. In general, the term "pharmaceutically acceptable salts" refer to salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (*J. Pharmaceutical Sciences*, 66; 1-19, 1977), incorporated herein by reference in its entirety, describes various pharmaceutically acceptable salts in details. Compound of Formula (I) can be used as such or in the form of its suitable salt. A reference to compound of Formula (I) is intended to include reference to such salts as well.

The term "infection" or "bacterial infection" as used herein includes presence of bacteria, in or on a subject, which, if its growth were inhibited, would result in a benefit to the subject. As such, the term "infection" in addition to referring to the presence of bacteria also refers to presence of normal floras, which are not desirable. The term "infection" includes infection caused by bacteria.

The term "subject" as used herein refers to vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise is at a risk of infection (preventing the bacterial infection). The term "therapeutic treatment" refers to administering treatment to a subject already suffering from infection. The terms "treat", "treating" or "treatment" as used herein also refer to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "administration" or "administering" includes delivery of a composition or one or more pharmaceutically active ingredients to a subject, including for example, by any appropriate methods, which serves to deliver the composition or its active ingredients or other pharmaceutically active ingredients to the site of the infection. The method of administration may vary depending on various factors, such as for example, the components of the pharmaceutical composition or the type/nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention include oral, intravenous, topical, intramuscular and parenteral. The compositions according to the invention may also be reconstituted and/or diluted prior to administration.

The compositions according to the invention may further comprise one or more pharmaceutically acceptable excipients. The term "pharmaceutically inert ingredient" or "carrier" or "excipient" refers to a compound or material used to facilitate administration of a compound, for example, to increase the solubility of the compound. Typical, non-limiting examples of solid excipients include, starch, lactose, dicalcium phosphate, sucrose, and kaolin. Typical, non-limiting examples of liquid excipients include sterile water and edible oils such as peanut oil and sesame oil. In addition, various adjuvants commonly used in the art may also be included. These and other such excipients are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press., which is incorporated herein by reference in its entirety.

The term "related substances" as used herein refers to one or more impurities present in the pharmaceutical composition according to the invention. Such impurities may be present in the composition due to degradation of one or more components in the composition, for example the active or inactive ingredients. The amount of impurities is calculated on the basis of the compound of Formula (I) or a pharmaceutically acceptable derivative thereof present in the composition.

The term "N-oxide impurity" as used herein refers to a compound of Formula (II):

Compound of Formula (II)

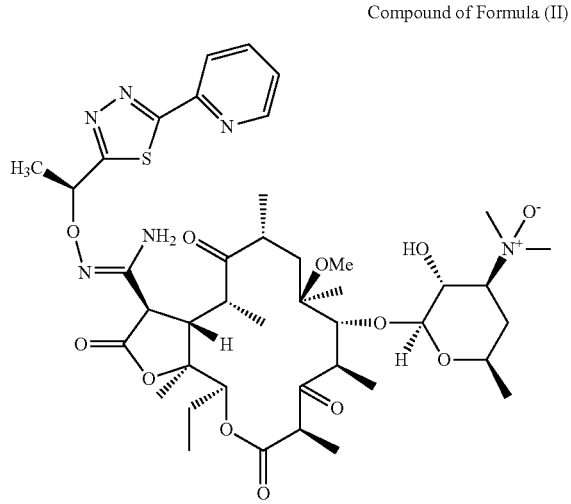

The term "N-demethyl impurity" as used herein refers to a compound of Formula (III):

Compound of Formula (III)

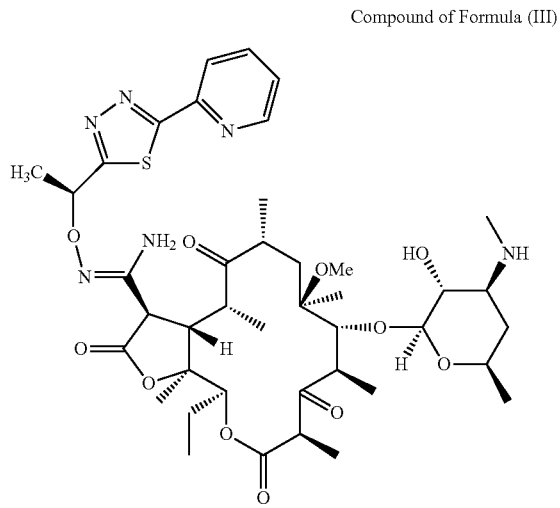 [SMILES: CC[C@@H]1OC(=O)[C@H](C)C(=O)[C@H](C)[C@@H](O[C@@H]2O[C@H](C)C[C@H](NC)[C@H]2O)[C@](C)(OC)C[C@@H](C)C(=O)[C@H](C)[C@H]2[C@H](/C(N)=N/O[C@@H](C)c3nnc(-c4ccccn4)s3)C(=O)O[C@@]21C]

The term "3-hydroxy impurity" as used herein refers to a compound of Formula (IV):

Compound of Formula (IV)

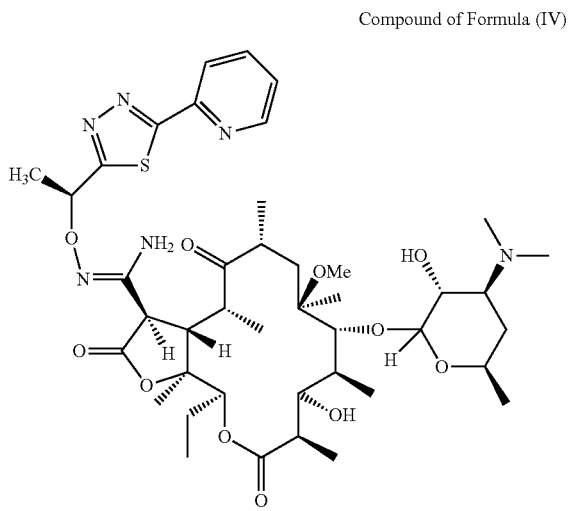

The term "isomer impurity" as used herein refers to a compound of Formula (V):

Compound of Formula (V)

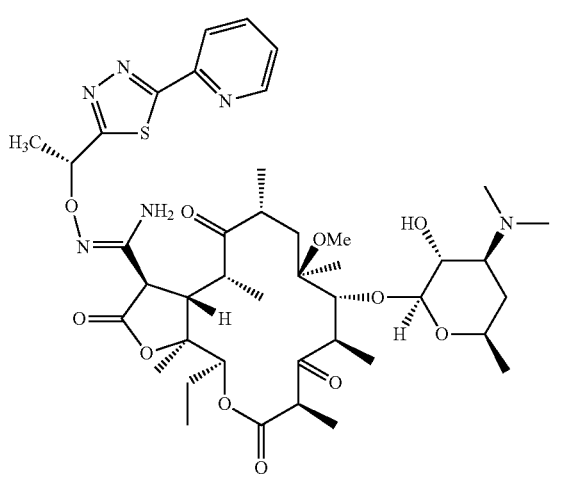

The term "epimer impurity" as used herein refers to a compound of Formula (VI):

Compound of Formula (VI)

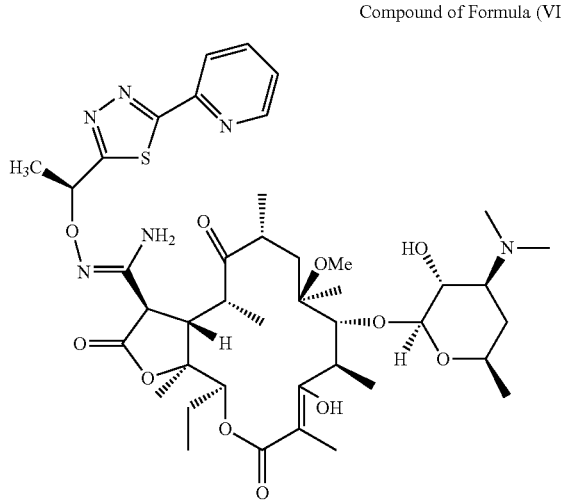

The compositions according to the invention are solid pharmaceutical compositions comprising a compound of Formula (I) or a pharmaceutically acceptable derivative thereof. The amount of compound of Formula (I) or a pharmaceutically acceptable derivative thereof in the compositions according to the invention can vary depending on various factors, including for example, the age of the subject, nature and extent of infection, desired therapeutic effect etc. In some embodiments, the compositions according to the invention comprise about 10 mg to about 2000 mg of a compound of Formula (I) or a pharmaceutically acceptable derivative thereof. In some other embodiments, the composition according to the invention comprises about 100 mg to about 1500 mg of a compound of Formula (I) or a pharmaceutically acceptable derivative thereof.

The pharmaceutical compositions according to the invention may include one or more pharmaceutically acceptable carriers or excipients or the like. Typical, non-limiting examples of such carriers or excipients include diluents, disintegrants, binders, wetting agents, emulsifying agents, solubilizing agents, buffering agents, glidants, lubricants, preservatives, stabilizing agents, flavoring agents and the like.

In some embodiments, there are provided pharmaceutical compositions comprising a compound of Formula (I) or a stereoisomer or a pharmaceutically acceptable derivative thereof as an active ingredient and one or more excipients selected from diluent, disintegrant, binder, lubricant or glidant.

The pharmaceutical compositions to the invention may be formulated into a variety of solid oral dosage forms. Typical, non-limiting examples of some oral dosage forms include tablet, capsule, powder, discs, caplets, pellets, granules, granules in capsule, minitablets, minitablets in capsule, pellets in capsule and the like. In some embodiments, the compositions according to invention may also be formulated into other dosage form suitable for oral administration such as suspensions, emulsions, syrups, elixirs and the like.

In some embodiments, compound of Formula (I) or a stereoisomer or a pharmaceutically acceptable derivative thereof present in the composition is in an amount within the range of from about 10% to about 90% by weight.

In some embodiments, diluent is present in an amount within the range of from about 1% to about 80% by weight. In some other embodiments, diluent is present in an amount within the range of from about 10% to about 50% by weight.

In some embodiments, disintegrant, if present, is present in an amount within the range of from about 0% to about 30% by weight. In some other embodiments, disintegrant is present in an amount within the range of from about 0.25% to about 15% by weight.

In some embodiments, binder, if present, is present in an amount within the range of from about 0% to about 30% by weight. In some other embodiments, binder is present in an amount within the range of from about 0.25% to about 10% by weight.

In some embodiments, glidant, if present, is present in an amount within the range of from about 0% to about 20% by weight. In some other embodiments, glidant is present in an amount within the range of from about 0.1% to about 5% by weight.

In some embodiments, lubricant, if present, is present in an amount within the range of from about 0% to about 20% by weight. In some other embodiments, lubricant is present in an amount within the range of from about 0.1% to about 5% by weight.

In some embodiments, the formulated tablets are coated with a suitable coating material dissolved in a suitable solvent. In some embodiments, coating is present in an amount within the range of from about 0.25% to about 10% by weight.

In some embodiments, the compositions according to the invention comprise: (a) a compound of Formula (I) or a pharmaceutically acceptable derivative thereof, (b) diluent, (c) binder, (d) disintegrant, (e) lubricant, and (f) glidant. In some embodiments, the composition according to invention is coated with a suitable coating agent.

In some embodiments, there are provided pharmaceutical compositions comprising:
a compound of Formula (I) or a stereoisomer or a pharmaceutically acceptable derivative thereof as an active ingredient in an amount between about 10% to about 90% by weight;
at least one or more diluent in an amount between about 10% to about 50% by weight;
optionally one or more disintegrant in an amount between about 0.25% to about 15% by weight;
optionally one or more binder in an amount between about 0.25% to about 10% by weight;
optionally one or more lubricant in an amount between about 0.1% to about 5% by weight;
optionally one or more glidant in an amount between about 0.1% to about 5% by weight;
optionally film coating in an amount between about 0.25% to about 10% by weight.

In some embodiments, the compositions according to the invention comprise: (a) a compound of Formula (I) or a pharmaceutically acceptable derivative thereof, (b) Microcrystalline cellulose, (c) Crosscarmellose sodium, (d) Povidone, (e) Talc, and (f) Magnesium stearate. In some embodiments, the composition according to invention is coated with Opadry.

In some embodiments, there are provided pharmaceutical compositions comprising:
(a) a compound of Formula (I) or a pharmaceutically acceptable derivative thereof in an amount between about 10% to about 90%;
(b) microcrystalline cellulose in an amount of about 10% to about 50% by weight;

(c) crosscarmellose in an amount of about 0.25% to about 15% by weight;
(d) povidone in an amount of about 0.25% to about 10% by weight;
(e) magnesium stearate in an amount of about 0.1% to about 5% by weight;
(f) talc in an amount of about 0.1% to about 5% by weight; and
(g) opadry film coating in an amount of about 0.25% to about 10% by weight.

Typical, non-limiting examples of diluents include microcrystalline cellulose, cellulose, lactose, starch, pregelatinized starch, corn starch, calcium carbonate, calcium sulfate, sugar, dextrates, sucrose, dextrin, fructose, dextrose, xylitol, polysaccharide, dibasic calcium phosphate dihydrate, tribasic calcium phosphate, calcium sulphate, kaolin, magnesium carbonate, magnesium oxide, maltodextrin, mannitol, polymethacrylates, potassium chloride, sodium chloride, sorbitol, and the like.

Typical, non-limiting example of binders include acacia, alginic acid, carbomer (carbopol), carboxymethylcellulose sodium, corn starch, dextrin, ethyl cellulose, methyl cellulose, gelatin, guar gum, hydrogenated vegetable oil, hydroxyethyl cellulose, hydroxypropylcellulose, hydroxypropylmethylcellulose, liquid glucose, magnesium aluminium silicate, maltodextrin, methyl cellulose, cellulose acetate, polymethacrylates, povidone, polyvinyl alcohol, pregelatinized starch, sodium alginate, starch, carnuba wax, paraffin, spermaceti, polyethylenes, microcrystalline wax and the like.

Typical, non-limiting examples of disintegrants include alginic acid, carboxymethylcellulose calcium, carboxymethylcellulose sodium, colloidal silicon dioxide, croscarmellose sodium, crospovidone, gura gum, low substituted hydroxypropyl cellulose, magnesium aluminium silicate, methyl cellulose, microcrystalline cellulose, polacrilin potassium, powdered cellulose, starch, pregelatinized starch, corn starch, potato starch, sodium alginate, sodium starch glycolate, and the like.

Typical, non-limiting examples of glidants include silicon dioxide, colloidal silicon dioxide, magnesium silicate, magnesium trisilicate, powdered cellulose, starch, talc, tribasic calcium phosphate and the like.

Typical non-limiting examples of lubricants include magnesium stearate, zinc stearate, calcium stearate, carnauba wax, palmitic acid, glyceryl monosterate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, myristic acid, talc, zinc stearate and the like.

In some embodiments, the compositions according to invention are coated with suitable coating polymers. Typical non-limiting examples of coating polymers include hydroxypropylmethyl cellulose, polyvinyl alcohol, ethyl cellulose, methacyrlic polymers, hydroxyproyl cellulose, starch and the like. In some embodiments, coating can optionally include a plasticizer. Typical, non-limiting examples of plasticizers include triacetin, diethyl phthalate, tributyl sebacate, polyethylene glycol, glycerin, triacetin, triethyl citrate and the like. In some embodiments, coating can also optionally include an anti-adherent or glidant. Typical, non-limiting examples of anti-adherent or glidant include talc, fumed silica, magnesium stearate and the like. In some other embodiments, coating can also optionally include an opacifier. Typical, non-limiting example of opacifier includes titanium dioxide and the like. In yet another embodiment, coating can also optionally include one or more colorants. In some embodiments, the compositions according to present invention are film coated with a suitable opadry coating material.

In some embodiments, the compositions according to the invention comprise: (a) about 100 mg to about 1500 mg of a compound of Formula (I) or a pharmaceutically acceptable derivative thereof, (b) about 50 mg to 1000 mg of Microcrystallline cellulose, (c) 10 mg to about 150 mg of Crosscarmellose sodium, (d) about 2 mg to about 75 mg of Povidone, (e) about 1 mg to about 30 mg of Talc, and (f) about 1 mg of 30 mg of Magnesium stearate. However, amounts beyond these ranges can also be employed as desired.

In some embodiments, the compositions according to the invention are formulated as tablets. Such tablets may be prepared using known techniques. In some embodiments, the compositions according to the invention are formulated as tablets by following dry granulation, wet granulation or direct compression techniques. In some embodiments, compositions according to the invention are formulated as tablets by following a wet granulation technique.

In some embodiments, there is provided a process for preparing the composition according to invention in the form of tablets; said process comprising:
(a) mixing a compound of Formula (I) or a stereoisomer or a pharmaceutically acceptable derivative thereof with one or more diluent and one or more disintegrant;
(b) wet granulating the mixture of step (a) in presence of a binder solution;
(c) drying and sieving the granulated mixture obtained in step (b);
(d) optionally blending the granulated mixture obtained in step (c) with one or more of a diluent, binder, disintegrant, glidant and lubricant;
(e) compressing the mixture obtained in step (c) or step (d) into tablets; and
(f) optionally film coating the formulated tablets.

In some embodiments, there is provided a process for preparing the composition according invention in the form of tablets; said process comprising:
(a) mixing a compound of Formula (I) or a stereoisomer or a pharmaceutically acceptable derivative thereof with microcrystalline cellulose and povidone;
(b) wet granulating the mixture of step (a) in presence of a binder solution comprising crosscarmellose sodium dissolved in water;
(c) drying and sieving the granulated mixture obtained in step (b);
(d) optionally blending the granulated mixture obtained in step (c) with crosscarmellose sodium, talc and magnesium stearate;
(e) compressing the mixture of step (c) or step (d) into tablets; and
(f) optionally film coating the formulated tablets.

In some embodiments, there are provided stable pharmaceutical compositions comprising a compound of Formula (I) or a stereoisomer or a pharmaceutically acceptable derivative thereof, wherein the composition exhibits a dissolution profile such that about 75% or more of a compound of Formula (I) or a stereoisomer or a pharmaceutically acceptable derivative thereof is released within 20 minutes, when measured using a USP Dissolution Apparatus II in 900 ml of 0.1 N HCl at a temperature of 37±0.5° C. and 50 rpm.

Advantageously, the compositions according to the invention are stable on storage, as assessed from the impurity content following storage at various conditions.

In some embodiments, the compositions according to the invention comprise less than about 2% w/w of total impurities following one or more of the following:
(i) storage for three months at a temperature of 40° C. (±2° C.) and a relative humidity of 75% (±5%); and
(ii) storage for three months at a temperature of 25° C. (±2° C.) and a relative humidity of 60% (±5%).

In some other embodiments, the compositions according to the invention comprise about 0.1% w/w to about 2% w/w of total impurities following one or more of the following:
(i) storage for three months at a temperature of 40° C. (±2° C.) and a relative humidity of 75% (±5%); and
(ii) storage for three months at a temperature of 25° C. (±2° C.) and a relative humidity of 60% (±5%).

In some embodiments, the compositions according to the invention comprise less than about 1% w/w of epimer impurity following one or more of the following:
(i) storage for three months at a temperature of 40° C. (±2° C.) and a relative humidity of 75% (±5%); and
(ii) storage for three months at a temperature of 25° C. (±2° C.) and a relative humidity of 60% (±5%).

In some embodiments, the compositions according to the invention comprise about 0.1% w/w to about 1% w/w of epimer impurity following one or more of the following:
(i) storage for three months at a temperature of 40° C. (±2° C.) and a relative humidity of 75% (±5%); and
(ii) storage for three months at a temperature of 25° C. (±2° C.) and a relative humidity of 60% (±5%).

In some other embodiments, the compositions according to the invention comprise less than about 0.1% w/w of N-oxide impurity following one or more of the following:
(i) storage for three months at a temperature of 40° C. (±2° C.) and a relative humidity of 75% (±5%); and
(ii) storage for three months at a temperature of 25° C. (±2° C.) and a relative humidity of 60% (±5%).

In some embodiments, the compositions according to the invention comprise about 0.001% w/w to about 0.1% w/w of N-oxide impurity following one or more of the following:
(i) storage for three months at a temperature of 40° C. (±2° C.) and a relative humidity of 75% (±5%); and
(ii) storage for three months at a temperature of 25° C. (±2° C.) and a relative humidity of 60% (±5%).

In some other embodiments, the compositions according to the invention comprise less than about 0.5% w/w of N-demethyl impurity following one or more of the following:
(i) storage for three months at a temperature of 40° C. (±2° C.) and a relative humidity of 75% (±5%); and
(ii) storage for three months at a temperature of 25° C. (±2° C.) and a relative humidity of 60% (±5%).

In some embodiments, the compositions according to the invention comprise about 0.005% w/w to about 0.5% w/w of N-demethyl impurity following one or more of the following:
(i) storage for three months at a temperature of 40° C. (±2° C.) and a relative humidity of 75% (±5%); and
(ii) storage for three months at a temperature of 25° C. (±2° C.) and a relative humidity of 60% (±5%).

In some embodiments, the compositions according to the invention comprise less than about 0.5% w/w of 3-hydroxy impurity following one or more of the following:
(i) storage for three months at a temperature of 40° C. (±2° C.) and a relative humidity of 75% (±5%); and
(ii) storage for three months at a temperature of 25° C. (±2° C.) and a relative humidity of 60% (±5%).

In some other embodiments, the compositions according to the invention comprise about 0.01% w/w to about 0.5% w/w of 3-hydroxy impurity following one or more of the following:
(i) storage for three months at a temperature of 40° C. (±2° C.) and a relative humidity of 75% (±5%); and
(ii) storage for three months at a temperature of 25° C. (±2° C.) and a relative humidity of 60% (±5%).

In some embodiments, the compositions according to the invention comprise less than about 0.5% w/w of the isomer impurity following one or more of the following:
(i) storage for three months at a temperature of 40° C. (±2° C.) and a relative humidity of 75% (±5%); and
(ii) storage for three months at a temperature of 25° C. (±2° C.) and a relative humidity of 60% (±5%).

In some embodiments, the compositions according to the invention comprise about 0.01% w/w to about 0.5% w/w of isomer impurity following one or more of the following:
(i) storage for three months at a temperature of 40° C. (±2° C.) and a relative humidity of 75% (±5%); and
(ii) storage for three months at a temperature of 25° C. (±2° C.) and a relative humidity of 60% (±5%).

The compositions according to the invention are useful treating a variety of bacterial infections. Typical, non-limiting examples of infections that can be treated using the compositions according to the invention include those resulting in pneumonia, otitis media, sinusitus, bronchitis, tonsillitis, mastoiditis, pharynigitis, rheumatic fever, glomerulonephritis, respiratory tract infections, skin and soft tissue infections, abscesses and osteomyelitis, puerperal fever, urinary tract infections, urethritis, cervicitis, sexually transmitted diseases, toxin diseases, ulcers, systemic febrile syndromes, Lyme disease, conjunctivitis, keratitis, dacrocystitis, disseminated *Mycobacterium avium* complex (MAC) disease, gastroenteritis, intestinal protozoa related to infections, odontogenic infections, cough related to infection, gas gangrene related to infection, and atherosclerosis related to infection.

Typical, non-limiting examples of infections in animals that can be treated using compositions according to the invention include bovine respiratory diseases related to infection by *Mannheimia haemolytica, Pasteurella multocida, Histophilus somni, Mycoplasma bovis* or *Bordetella* spp.; cow enteric disease related to infection by *Escherichia coli* or protozoa (i.e., coccidia, cryptosporidia, etc.); dairy cow mastitis related to infection by *Staphylococcus aureus, Streptococcus uberis, Streptococcus agalactiae, Streptococcus dysgalactiae, Klebsiella* spp., *Corynebacterium*, or *Enterococcus* spp.; swine respiratory disease related to infection by *Actinobacillus* pleuropneumonia, *Pasteurella multocida*, or *Mycoplasma* spp.; swine enteric disease related to infection by *E. coli, Lawsonia intracellularis, Salmonella*, or *Serpulinahyodyisinteriae*; cow footrot related to infection by *Fusobacterium* spp.; cow metritis related to infection by *Escherichia coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *Escherichia coli*; skin and soft tissue infections in dogs and cats related to infection by *Staphylococcus epidermidis, Staphylococcus intermedius*, Coagulase negative Staphylococci or *Pasteurella multocida*; and dental or mouth infections in dogs and cats related to infection by *Alcaligenes* spp., *Bacteroides* spp., *Clostridium* spp., *Enterobacter* spp., *Eubacterium, Peptostreptococcus, Porphyromonas*, or *Prevotella*.

In general, the compositions according to the invention are useful in treating infections caused by various microorganisms. In some embodiments, compositions according to the invention are useful in treating infections caused by *Staphylococcus* spp., *Streptococcus* spp., *Haemophilus* spp., *Moracella* spp., *Legionella* spp., *Chlamydia* spp., *Clostridium* spp. or *Mycoplasma* spp. Typical, non-limiting examples of *Staphylococcus* spp. include *Staphylococcus aureus, Staphylococcus epedermidis, Staphylococcus saprophyticus* and the like. Typical, non-limiting examples of *Streptococcus* spp. include *Streptococcus agalactiae, Streptococcus anginosus, Streptococcus bovis, Streptococcus canis, Streptococcus constellatus, Streptococcus dysgalactiae, Streptococcus equinus, Streptococcus iniae, Streptococcus intermedius, Streptococcus milleri, Streptococcus mitis, Streptococcus mutans, Streptococcus oralis, Streptococcus parasanguinis, Streptococcus peroris, Streptococcus pneumoniae, Streptococcus pseudopneumoniae, Streptococcus pyogenes, Streptococcus ratti, Streptococcus salivarius, Streptococcus tigurinus, Streptococcus thermophilus, Streptococcus sanguinis, Streptococcus sobrinus, Streptococcus suis, Streptococcus uberis, Streptococcus vestibularis, Streptococcus zooepidemicus*, Groups C and G streptococci, *Viridans streptococci*, Groups A, B, and C streptococci, Streptococcal groups C-F (minute-colony streptococci), and the like. Typical, non-limiting examples of *Haemophilus* spp. include *Haemophilus aegyptius, Haemophilus aphrophilus, Haemophilus avium, Haemophilus ducreyi, Haemophilus felis, Haemophilus haemolyticus, Haemophilus influenzae, Haemophilus parainfluenzae, Haemophilus paracuniculus, Haemophilus parahaemolyticus, Haemophilus pittmaniae, Haemophilus segnis, Haemophilus somnus* and the like. Typical, non-limiting examples of *Moracella* spp. include *Moracella atlantae, Moracella boevrei, Moracella bovis, Moracella bovoculi, Moracella canis, Moracella caprae, Moracella catarrhalis, Moracella caviae, Moracella cuniculi, Moracella equi, Moracella lacunata, Moracella lincolnii, Moracella nonliquefaciens, Moracella oblonga, Moracella osloensis, Moracella pluranimalium, Moracella porci* and the like. Typical, non-limiting example of *Legionella* spp. include *Legionella adelaidensis, Legionella anisa, Legionella beliardensis, Legionella birminghamensis, Legionella bozemanae, Legionella brunensis, Legionella busanensis, Legionella cardiaca, Legionella cherrii, Legionella cincinnatiensis, Legionella donaldsonii, Legionella drancourtii, Legionella dresdenensis, Legionella drozanskii, Legionella dumoffii, Legionella erythra, Legionella fairfieldensis, Legionella fallonii, Legionella feeleii, Legionella geestiana, Legionella gormanii, Legionella gratiana, Legionella gresilensis, Legionella hackeliae, Legionella impletisoli, Legionella israelensis, Legionella jamestowniensis, Legionella jeonii, Legionella jordanis, Legionella lansingensis, Legionella londiniensis, Legionella longbeachae, Legionella lytica, Legionella maceachernii, Legionella massiliensis, Legionella micdadei, Legionella monrovica, Legionella moravica, Legionella nagasakiensis, Legionella nautarum, Legionella oakridgensis, Legionella parisiensis, Legionella pittsburghensis, Legionella pneumophila, Legionella quateirensis, Legionella quinlivanii, Legionella rowbothamii, Legionella rubrilucens, Legionella sainthelensi, Legionella santicrucis, Legionella shakespearei, Legionella spiritensis, Legionella steelei, Legionella steigerwaltii, Legionella taurinensis, Legionella tucsonensis, Legionella tunisiensis, Legionella wadsworthii, Legionella waltersii, Legionella worsleiensis, Legionella yabuuchiae* and the like. Typical non-limiting examples of *Chlamydia* spp. include *Chlamydia muridarum, Chlamydia philapecorum, Chlamydia suis, Chlamydia trachomatis, Chlamydia pneumoniae* and the like. Typical non-limiting examples of *Clostridium* spp. include *Clostridium diptheriae, Clostridium perfringens* and the like. Typical non-limiting examples of *Mycoplasma* spp. include *Mycoplasma amphoriforme, Mycoplasma buccale, Mycoplasma faucium, Mycoplasma fermentans, Mycoplasma genitalium, Mycoplasma hominis, Mycoplasma lipophilum, Mycoplasma orale, Mycoplasma penetrans, Mycoplasma pirum, Mycoplasma pneumoniae, Mycoplasma primatum, Mycoplasma salivarium, Mycoplasma spermatophilum* and the like.

In some embodiments, compositions according to the invention are useful in treating infections caused by *Peptostreptococcus* spp., *Actinobacillus haemolyticum, Mycoplasma pneumoniae, Corynebacterium minutissimum, Bartonella henselae; Enterococcus* spp., *Treponema pallidum, Ureaplasma urealyticum, Neiserria gonorrheae; Helicobacter pylori; Borrelia recurrentis; Borrelia burgdorferi; Listeria* spp., *Mycobacterium avium* complex (MAC) *Mycobacterium avium, Mycobacterium intracellulare, Campylobacter jejuni; Cryptosporidium* spp.; *Bordetella pertussis; Bacteroides* spp. and the like.

In some embodiments, there is also provided a method for treating bacterial infection in a subject, said method comprising administering to said subject a therapeutically effective amount of a pharmaceutical composition according to invention.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

The pharmaceutical compositions according to invention are formulated as tablets. Table 1 provides the qualitative and quantitative compositions according to the invention.

TABLE 1

Pharmaceutical compositions according to the invention

| | | mg/Tablet | |
|---|---|---|---|
| Sr. | Ingredients | Example 1 | Example 2 |
| | INTRAGRANULAR | | |
| 1 | Compound of Formula (I) | 200.0 | 400.0 |
| 2 | Microcrystalline Cellulose (Avicel PH 101) | 80.0 | 160.0 |
| 3 | Croscarmesllose Sodium (Ac-Di-Sol) | 7.0 | 14.0 |

TABLE 1-continued

Pharmaceutical compositions according to the invention

| Sr. | Ingredients | mg/Tablet Example 1 | mg/Tablet Example 2 |
|---|---|---|---|
| 4 | Povidone K30 (Kollidone K30) | 8.75 | 17.50 |
| 5 | Purified water USP | q.s. | q.s. |
| | EXTRAGRANULAR | | |
| 6 | Microcrystalline cellulose (Avicel PH 102) | 31.25 | 62.50 |
| 7 | Croscarmesllose Sodium (Ac-Di-Sol) | 13.0 | 26.0 |
| 8 | Talc | 3.50 | 7.00 |
| 9 | Magnesium stearate | 3.0 | 6.0 |
| | CORE TABLET (mg) | 350.0 | 700.0 |
| | FILM COATING | | |
| 10 | Opadry Yellow (03B28796) | 10.5 | 21.0 |
| 11 | Purified Water USP | q.s. | q.s. |
| | Total (Coated Tablet Weight) mg | 360.50 | 721.0 |

Manufacturing Procedure:

The compound of Formula (I) ((11S,21R)-3-decladinosyl-11,12-dideoxy-6-O-methyl-3-oxo-12,11-{oxycarbonyl-[Z—N-[1-(5-pyridin-2-yl-1,3,4-thiadiazol-2-yl)-(S)-ethoxy]-carboxamidino]methylene}-erythromycin A), microcrystalline cellulose, crosscarmellose sodium were weighed, sifted, and mixed in a Rapid Mixer Granulator. The above mass was granulated by spraying aqueous solution of povidone. The granules were dried in a fluidized bed drier, sifted and milled. The resulting granules were blended with sifted microcrystalline cellulose, crosscarmellose sodium, talc and magnesium stearate. The lubricated granules were compressed into tablets using suitable tooling. The tablets were coated with aqueous dispersion of opadry.

TABLE 2

Dissolution profile of compositions according to the invention

| Time | % Drug release | |
|---|---|---|
| (min) | Example 1 | Example 2 |
| 5 | 97 | 92 |
| 10 | 100 | 97 |
| 15 | 100 | 100 |
| 20 | 100 | 100 |
| 30 | 100 | 101 |
| 45 | 100 | 101 |
| 60 | 100 | 102 |

The compositions according to invention were tested for their in-vitro release profile of an active ingredient. Table 2 provides the dissolution profile for the tablets comprising a compound of Formula (I) (as mesylate salt) prepared as per compositions given in Table 1. The drug release rate was determined using USP Dissolution Apparatus II in 900 ml of 0.1 N HCl at a temperature of 37±0.5° C. and paddles rotated at 50 rpm. As seen from the results of Table 2, the compositions according to invention exhibited immediate release profile of an active ingredient.

The compositions according to invention were also tested for stability up to three months at various conditions: (a) 25° C. temperature and 60% relative humidity; and (b) 40° C. temperature and 75% relative humidity. The results of the stability studies are provided in Tables 3 to 4.

TABLE 3

Stability data of composition according to Example 1

| Parameter | Initial | 40° C./75% RH | | | 25° C./60% RH |
|---|---|---|---|---|---|
| | | Months | | | |
| | 0 Month | 1 Month | 2 Month | 3 Month | 3 Month |
| Assay % w/w) (by HPLC) | 95.8 | 94.1 | 93.7 | 94.6 | 97.6 |
| Water by KF (% W/w) | 3.78 | 2.92 | 2.84 | 3.66 | 3.62 |

Dissolution: Method: 0.1N HCl, 900 ml, USP II, 50 rpm

| Time (minutes) | % drug dissolved | | | | |
|---|---|---|---|---|---|
| 5 | 97 | 95 | 95 | 100 | 97 |
| 10 | 100 | 97 | 98 | 102 | 96 |
| 15 | 100 | 99 | 98 | 103 | 97 |
| 20 | 100 | 98 | 99 | 103 | 99 |
| 30 | 100 | 98 | 100 | 103 | 100 |
| 45 | 100 | 99 | 100 | 103 | 101 |
| 60 | 100 | 99 | 101 | 103 | 102 |

Related Substances (% w/w) (By HPLC)

| Substance A | 0.020 | 0.011 | 0.013 | 0.007 | 0.005 |
|---|---|---|---|---|---|
| Substance B | 0.065 | 0.000 | 0.000 | 0.041 | 0.034 |
| Substance C | 0.054 | 0.056 | 0.055 | 0.046 | 0.045 |
| Substance D | 0.106 | 0.075 | 0.076 | 0.094 | 0.098 |
| Substance E | 0.316 | 0.339 | 0.373 | 0.320 | 0.313 |
| Substance F | 0.000 | 0.000 | 0.000 | 0.000 | 0.000 |
| Highest Unknown Impurity | 0.231 | 0.220 | 0.219 | 0.219 | 0.221 |
| Total Unknown Impurity | 0.302 | 0.380 | 0.341 | 0.313 | 0.321 |
| Total Related Substances | 0.863 | 0.861 | 0.858 | 0.821 | 0.816 |

TABLE 4

Stability data of composition according to Example 2

| Parameter | | | | | |
|---|---|---|---|---|---|
| | Initial | 40° C./75% RH | | | 25° C./60% RH |
| | | Months | | | |
| | 0 Month | 1 Month | 2 Month | 3 Month | 3 Month |
| Assay (% w/w) (by HPLC) | 96.7 | 96.9 | 94.9 | 95.4 | 94.8 |
| Water by KF (% w/w) | 4.07 | 2.47 | 2.69 | 2.6 | 2.76 |
| Dissolution: Method: 0.1N HCl, 900 ml, USP II, 50 rpm | | | | | |
| Time (minutes) | % drug dissolved | | | | |
| 5 | 92 | 90 | 93 | 96 | 95 |
| 10 | 97 | 95 | 98 | 97 | 96 |
| 15 | 100 | 96 | 99 | 98 | 99 |
| 20 | 100 | 97 | 100 | 99 | 100 |
| 30 | 101 | 97 | 100 | 100 | 101 |
| 45 | 101 | 100 | 101 | 101 | 101 |
| 60 | 102 | 101 | 101 | 101 | 101 |
| Related Substances (% w/w) (By HPLC) | | | | | |
| Substance A | 0.015 | 0.017 | 0.014 | 0.013 | 0.011 |
| Substance B | 0.057 | 0.061 | 0.000 | 0.000 | 0.000 |
| Substance C | 0.052 | 0.054 | 0.060 | 0.049 | 0.048 |
| Substance D | 0.114 | 0.097 | 0.075 | 0.076 | 0.075 |
| Substance E | 0.347 | 0.363 | 0.383 | 0.375 | 0.343 |
| Substance F | 0.000 | 0.000 | 0.000 | 0.000 | 0.000 |
| Highest Unknown Impurity | 0.23 | 0.217 | 0.219 | 0.220 | 0.220 |
| Total Unknown Impurity | 0.304 | 0.297 | 0.322 | 0.335 | 0.324 |
| Total Related Substances | 0.889 | 0.889 | 0.854 | 0.848 | 0.801 |

The invention claimed is:

1. A solid pharmaceutical composition comprising: (a) a compound of Formula (I):

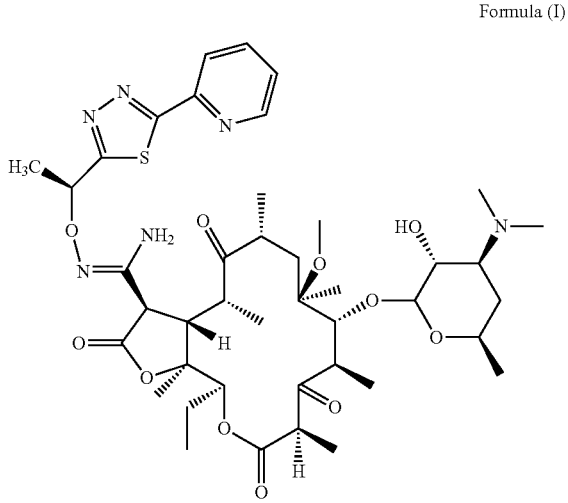 [SMILES: CC[C@@H]1OC(=O)[C@H](C)C(=O)[C@H](C)[C@@H](OC2O[C@H](C)C[C@H](N(C)C)[C@H]2O)[C@](C)(OC)C[C@@H](C)C(=O)[C@H](C)[C@H]2[C@H](/C(N)=N/O[C@@H](C)c3nnc(-c4ccccn4)s3)C(=O)O[C@@]21C]

Formula (I)

or a stereoisomer or a pharmaceutically acceptable salt thereof, (b) microcrystalline cellulose, (c) crosscarmellose sodium, (d) povidone, (e) talc, and (f) magnesium stearate; wherein said composition is in form of tablets.

2. The composition according to claim 1, comprising: (a) about 100 mg to about 1500 mg of a compound of Formula (I) or a pharmaceutically acceptable salt thereof, (b) about 50 mg to 1000 mg of microcrystalline cellulose, (c) 10 mg to about 150 mg of Crosscarmellose sodium, (d) about 2 mg to about 75 mg of Povidone, (e) about 1 mg to about 30 mg of Talc, and (f) about 1 mg of 30 mg of Magnesium stearate.

3. A pharmaceutical composition according to claim 1, wherein the composition exhibits a dissolution profile such that about 75% or more of a compound of Formula (I) or a stereoisomer or a pharmaceutically acceptable salt thereof is released within 20 minutes, when measured using a USP Dissolution Apparatus II in 900 ml of 0.1 N HCl at a temperature of 37±0.5° C. and 50 rpm.

* * * * *